United States Patent [19]

Fredricks

[11] 4,016,865

[45] Apr. 12, 1977

[54] CERVICAL-VAGINAL SPATULA

[76] Inventor: Richard N. Fredricks, 201 E. 28th St., New York, N.Y. 10016

[22] Filed: Sept. 17, 1975

[21] Appl. No.: 614,314

[52] U.S. Cl. .............................. 128/002 B; 128/304
[51] Int. Cl.$^2$ .................. A61B 10/00; A61B 17/22
[58] Field of Search ........................ 128/002 B, 304

[56] References Cited

UNITED STATES PATENTS

| | | | |
|---|---|---|---|
| 2,471,088 | 5/1949 | Ayre | 128/2 B |
| 3,315,661 | 4/1967 | Groat | 128/2 B |
| 3,352,299 | 11/1967 | Sagiroglu | 128/2 B |
| 3,485,236 | 12/1969 | Frost | 128/2 B |
| 3,554,185 | 1/1971 | Kohl | 128/2 B |
| 3,633,565 | 1/1972 | McDonald | 128/304 X |
| D210,757 | 4/1968 | Michel | 128/2 B UX |

Primary Examiner—Channing L. Pace
Attorney, Agent, or Firm—Natter & Natter

[57] ABSTRACT

A planar cervical-vaginal cytological spatula includes a flat manipulating stem with an endocervical sampling head at one end and a broad vaginal sampling head at the other end. The endocervical head includes a wedge shaped forward protuberance adapted for insertion into the endocervical canal. A first edge of the protuberance is coincident with a straight lateral edge of the stem and terminates at a rounded tip of a diameter approximating that of a normal cervical canal. The other edge of the protuberance slopes angularly away from the tip toward the stem at an angle in the order of 18° from the first edge and terminates with a transverse base dimension in the order of twice the diameter of a normal cervical canal at the cervical portio. From the wedge base the sloped edge leads to an undulated transverse squamous sampling surface extending perpendicular to the axis of the stem.

7 Claims, 5 Drawing Figures

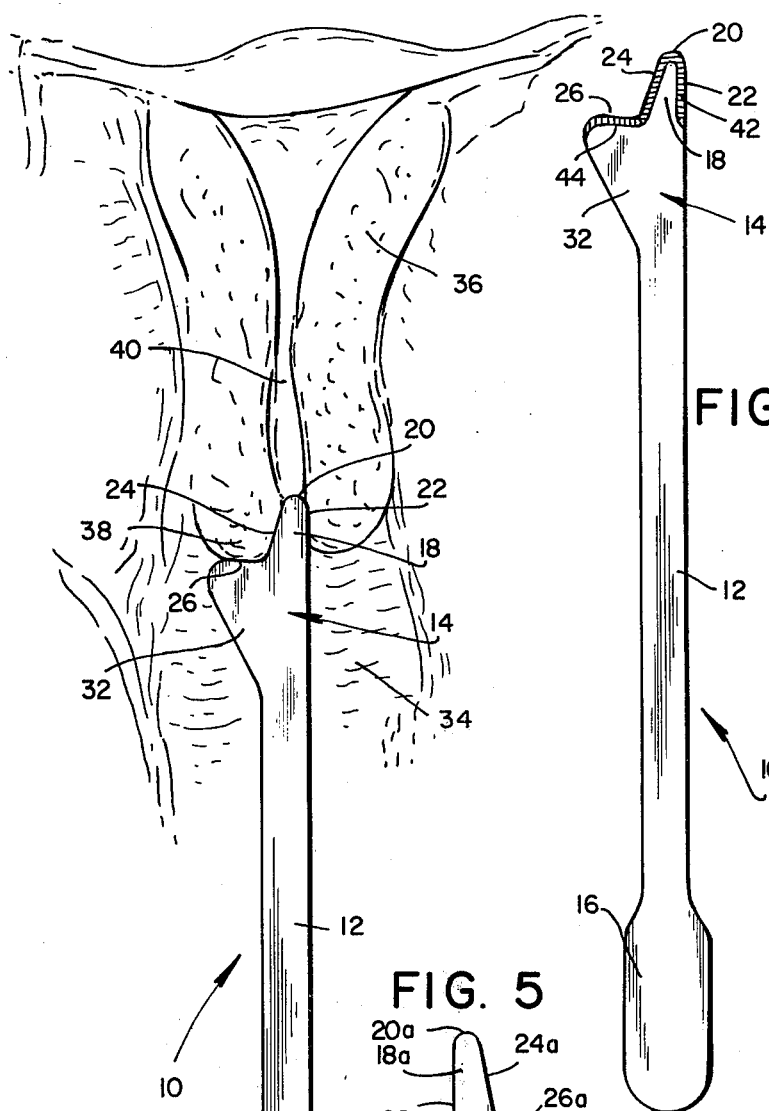
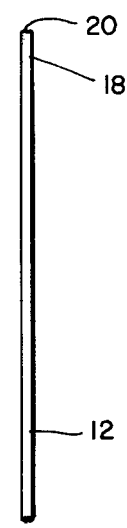
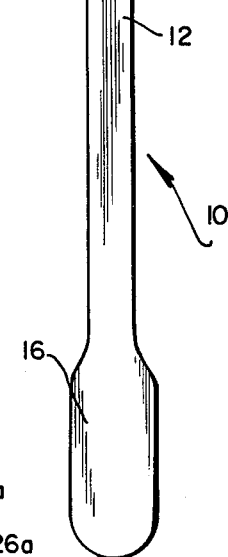
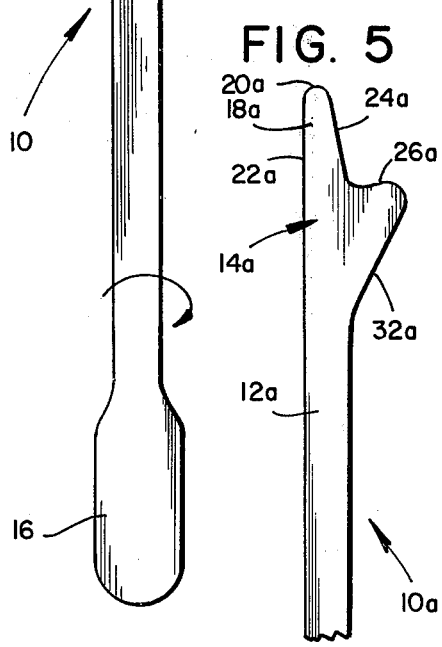
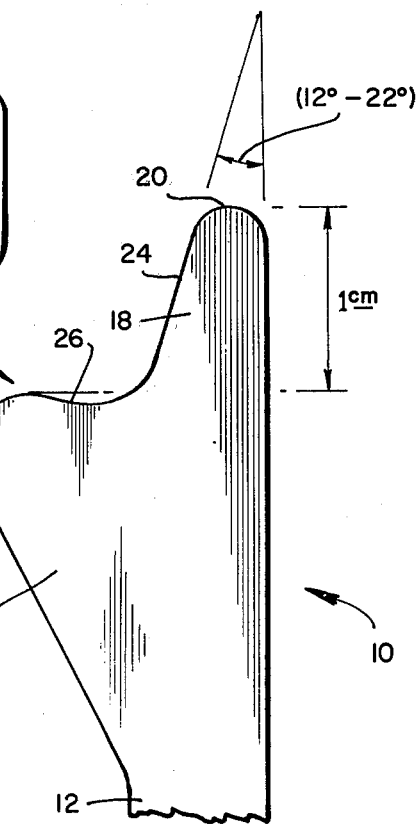

CERVICAL-VAGINAL SPATULA

BACKGROUND OF THE INVENTION

1. Field of the Invention

The invention relates generally to cervical specimen collecting devices and more particularly to a cytological specimen scraper or spatula.

2. Brief Description of the Prior Art

Cytological specimen samplers have been employed to obtain cervical-vaginal specimens by scraping the cervical region with a bladed spatula. Among the commonly used samplers was the cervical scraper described in U.S. Pat. No. 2,471,088, issued to Dr. James Ernest Ayre. This scraper was designed with a heart shaped tip comprised of a pair of divergent peaks, both offset from the axis of a stem in opposite directions. In use, one of the peaks was positioned against the cervical orifice, and the scraper was rotated while held in such position allowing the other peak to lightly scrape the circumference of the cervical lip.

A substantial number of cytological specimens obtained with scrapers such as the Ayre scraper did not indicate cells of endocervical origin and a swab was often conjunctively employed to obtain an endocervical sampling. Utilization of the scraper-swab technique, however, still did not achieve adequate endocervical samplings and an average of 50% of the specimens examined at processing laboratories did not contain endocervical cells. This fact is of major significance because it has been determined that a majority of early cervical carcinomas begin in the canal above the upper limits of the squamous epithelium and for this reason a satisfactory specimen for cytological analysis must contain cells of endocervical origin.

Studies have revealed that the area of transition or transition zone between the histologic portio and the endocervix provides endocervical cells and is therefore of particular pathological importance. Thus, the transition zone has become the target area for obtaining an adequate cytological specimen.

The broad pivotal tip of the Ayre spatula did not function to permit adequate penetration into the transition zone due to both its relatively short length and its broad span. Furthermore, manipulation of the spatula itself was awkward since the stem or rotating axis was offset with respect to the pivotal tip. When attempts were made to rotate the spatula about a fixed axis of rotation, the offset tip generated a broad circular path displacing the cervix and often produced hemorrhaging and trauma.

Returning to the recognition of the transition zone as the target area for specimen samplings, it has been determined that the zone varies in length and position and generally ascends the canal as the patient's age increases. This presented even further difficulties with respect to the use of the Ayre spatula because penetration of its broad tip was hampered due to the decreased elasticity of atrophic cervixes.

After some of the foregoing problems were appreciated attempts were made at providing modified scraper designs which would permit penetration deeper into the canal. An example of such attempts was illustrated in U.S. Pat. No. 3,352,299 wherein an elongate slender semi-eliptical scraper tip was designed for insertion into the canal. The use of scrapers of such configuration has not been widespread due to the increased incidence of hemorrhaging associated with the relatively pointed tip and the trauma inherent with deep penetration particularly when sharp implements were employed. Further, when such implement was inserted and inward pressure exerted against the face of the cervical portio, deflection of the cervix became a significant problem and adequate specimens could not be obtained without the exercise of a high degree of skill.

A further problem with regard to such scrapers was that since the protuberance was slender and long the scraper could not be fabricated of wood without the danger of possible tip fracture during manipulation within the canal and such scrapers were therefore restricted to plastics which resulted in higher costs and presented a sampling surface to which specimens did not readily adhere.

SUMMARY OF THE INVENTION

In compendium, a planar cervical spatula is formed with an endocervical head at one end of a stem and a vaginal head at the other. The endocervical head includes a wedge shaped forward protuberance adapted for endocervical cell sampling by insertion into and distension of the cervical canal with but minimal disturbance. The tip of the protuberance is of a diameter approximating that of the cervical canal at the cervical portio. The sides of the protuberance gradually expand to a transverse base dimension approximately twice that of the canal diameter so that when inserted into the canal lateral pressure is exerted against the cervical mucosa. A concave-convex squamous cell sampling web extends laterally from the base of the protuberance to provide a limit stop and cradle the cervical portio. Rotation of the scraper provides an adequate deposit of endocervical cells on the protuberance and of squamous cells on the web.

From the foregoing summary, it will be appreciated that it is an object of the present invention to provide a cervical-vaginal sampling spatula of the general character described which is not subject to the disadvantages aforementioned.

A further object of the present invention is to provide a cervical-vaginal sampling spatula of the general character described which is simple in construction, low in cost, reliable in use, and well adapted for mass production fabrication techniques.

Another object of the present invention is to provide a cervical-vaginal sampling spatula of the general character described which is capable of simultaneously obtaining cytological specimens of endocervical and squamous cell origin while minimizing attendant trauma.

Yet another object of the present invention is to provide a cervical-vaginal sampling spatula of the general character described which is adapted for easy penetration into and effective sampling distension of the transition zone of the cervical canal.

Yet another object of the present invention is to provide a cervical-vaginal sampling spatula of the general character described which is particularly adapted for obtaining endocervical cell specimens from the transition zone while at the same time being configured as to be safely fabricated of wood.

Other objects of the invention in part will be apparent and in part will be pointed out hereinafter.

With these ends in view, the invention finds embodiment in certain combinations of elements and arrangements of parts by which the objects aforementioned and certain other objects are hereinafter attained, all as fully described with reference to the accompanying drawings, and the scope of which is more particularly pointed out and indicated in the appended claims.

BRIEF DESCRIPTION OF THE DRAWINGS

In the accompanying drawings in which are shown some of the various possible exemplary embodiments of the invention:

FIG. 1 is a frontal sectional view through the vagina and uterus and illustrating a cervical-vaginal specimen spatula constructed in accordance with and embodying the invention in situ and positioned with a wedge protuberance seated in the cervical canal and with a direction arrow indicating the typical manipulation of the spatula for cytological specimen sampling;

FIG. 2 is an elevational view of the spatula illustrated in FIG. 1 after removal from the sampling position and indicating, in schematized fashion, the cytological specimens which have been deposited;

FIG. 3 is a fragmentary side view of the spatula;

FIG. 4 is a greatly enlarged fragmentary elevational view of the endocervical sampling head of the spatula and more clearly illustrating the anatomic surfaces of the wedge protuberance and a transverse squamous cell sampling web; and FIG. 5 is a fragmentary view of an alternate embodiment of the invention, the same having a modified endocervical head wherein the protuberance is extended in length for deeper penetration into the canal.

DESCRIPTION OF THE PREFERRED EMBODIMENTS

Referring now in detail to the drawings wherein the reference numeral 10 denotes an endocervical scraper constructed in accordance with and embodying the invention, the scraper 10 generally comprises a flat planar body incorporating a stem 12 having at one end an endocervical head 14 and at the other end a broad vaginal sampling head 16.

The vaginal head 16 is of conventional configuration having a width approximately twice the width of the stem and including a generally rounded tip. The head 16 is utilized to obtain a vaginal cell cytology specimen by manipulation thereof in the vaginal pool area and subsequent transfer of the specimen deposited on the head 16 to a suitable slide for analysis, all in a manner well known to skilled medical personnel.

A principal feature of the present invention resides in the configuration of the endocervical head 14 designed with anatomic criteria such that in routine use a sampling of cells of endocervical origin will be deposited thereon as a result of simple manipulation and while minimizing trauma and hemorrhaging normally attendant such samplings when prior art devices were utilized.

With reference to FIGS. 1 and 4, it will be seen that the endocervical head 14 includes a generally wedge shaped forward protuberance 18 having a rounded distal tip 20. A first straight scraping edge 22 of the protuberance is coincident with a straight lateral edge of the stem 12 and leads tangentially to the rounded distal tip 20 while a second straight scraping edge 24 slopes tangentially from the tip 20 toward the stem at an angle in the order of 18° from the edge 22. The second edge 24 extends along a straight line to the base of the wedge protuberance 18 which is of a transverse dimension in the order of twice the diameter of a normal cervical canal at the cervical portio. Commencing at approximately the wedge base, the second edge 24 leads to an undulated concave-convex squamous sampling edge 26 which extends generally transverse to the axis of the stem.

The squamous sampling edge 26 is the upper edge of a generally triangular web 32 forming a supportive base for the endocervical head 14, all of which is formed of one piece construction with the scraper body. In order to permit free rotative manipulation of the scraper within the vaginal cavity, the maximum width of the head 14 at the web 32 is approximately 1.5 centimeters.

It will be appreciated that for both safety and ease in insertion into the cervical canal the distal tip 20 of the endocervical head 14 is of a diameter not appreciably exceeding the normal diameter of an average cervical canal. Thus, it has been determined that the optimum diameter of the tip 20 is within a range of 3 to 5 millimeters.

To assure adequate distension of the cervical canal and therefore the deposit of an adequate endocervical specimen on the edges 22, 24 of the protuberance 18, the transverse base dimension of the protuberance 18 is in the order of twice the diameter of a normal cervical canal at the cervical portio and within a range of approximately 6 to 9 millimeters.

To insure penetration of the wedge protuberance 18 at least into the transition zone, the distance between the distal tip 20 and the squamous sampling edge 26 is at least one centimeter as illustrated in FIG. 4.

The angular orientation between the scraping edges 22, 24 of the wedge protuberance 18 conforms with the anatomical transverse base and tip dimensions of the protuberance and is approximately 18°, however it will be appreciated that variations are possible without departing from the invention and it is believed that satisfactory results are obtainable with wedge angles from 12° to 22°.

With reference now to FIG. 1 wherein the scraper 10 is shown in situ within a vaginal cavity 34 with the endocervical head 14 prepared for rotative scraping of the cervix for the removal of suitable cytological specimens, it will be observed that the reference numeral 36 denotes the uterus, the numeral 38 the cervix, and the numeral 40 the endocervical canal. In operation, the scraper 10 is inserted into the vaginal cavity 34 with the endocervical head 14 leading and the wedge protuberance 18 initially positioned at the cervical portio. Since the rounded distal tip 20 of the protuberance 18 is of a diameter approximating that of the cervical canal, the protuberance 18 may be easily introduced into the canal without the utilization of lubricants which might interfere with laboratory analysis of the specimens. Further penetration is accomplished while minimizing trauma because of the but gradual distension of the endocervical canal while the edge 24 gently exerts lateral pressure on the cervical mucosa.

With the protuberance 18 fully inserted, the concave portion of the squamous sampling edge 26 is seated against the cervical lip which provides an abutment stop limiting further penetration of the protuberance. In this position the protuberance 18 extends a distance of at least 1 centimeter into the canal, well within the transition zone of the canal, so that upon manipulative rotation of the scraper 10 abut the axis of the stem 12, as diagramatically illustrated by the arrow in FIG. 1, the edges 22 and 24 of the protuberance 18 will scrape the walls of the endocervical canal in the transition zone thus depositing a suitable specimen of cells of endocervical origin on the flat, front and rear faces of the endocervical head 14 adjacent the scraping edges 22, 24.

Simultaneously with the deposit of cells of endocervical origin, i.e. endocervical and/or metaplastic cells, on the flat parallel faces of the protuberance 18, the squamous sampling edge 26, cradling the cervical lip and circumscribing same during rotation of the scraper 10, scrapes the cervical lip and deposits a sampling of squamous cells on the flat parallel faces of the web support 32 adjacent the squamous sampling edge 26.

In FIG. 2 the scraper 10 illustrated in FIG. 1 is shown removed from the vaginal cavity and prior to the transfer of the specimens onto suitable slides which is done in the conventional manner. In diagramatic fashion, a typical deposit of endocervical material 42 is shown in a zone denoted for the purpose of illustration only by a plurality of parallel horizontal markings and a deposit of squamous material 44 is shown in a zone denoted for the purpose of illustration only by a series of vertical parallel markings. It should be appreciated that said markings have no bearing with respect to the actual appearance of the respective specimens deposited.

A further embodiment of the invention is illustrated in FIG. 5 wherein like numerals designate like components of the previous embodiment however bearing the suffix "a" after respective numerical designations. In this embodiment a scraper 10a is identical to the scraper 10 previously described except for the configuration of the endocervical head 14a.

The wedge protuberance 18a of the head 14a extends from its base to its distal tip 20a a length of approximately 1.5 centimeters while the distal tip 20a is a diameter approximating that of a normal cervical canal, e.g. 3 mm., and the angular orientation between the edges 22a and 24a in the order of 13° to 22°.

It should be appreciated that the protuberance 18a base dimension will therefore be somewhat greater than twice the diameter of a normal cervical canal and the endocervical head 14a of this embodiment is adapted for utilization in instances wherein the transition zone is not readily accessible utilizing the wedge protuberance 18 of the prior embodiment.

The scraper of the present invention is adapted for one piece construction of wood having a thickness in the order of 2 millimeters or less and due to the width of the protuberance at the base and the configuration of the web support 32 fracture of the protuberance and or web during manipulation is minimized. Thus, the scraper need not be fabricated of plastic which necessitates increased costs as well as difficulties with specimen adhesion. Furthermore, the utilization of wood construction facilitates economical mass fabrication with relatively low tooling costs.

Thus, it will be seen that there is provided a cervical scraper which achieves the various objects of the invention and which is well adapted to meet the conditions of practical use.

Since various possible embodiments might be made of the present invention and since various changes might be made in the exemplary embodiments above set forth, it is to be understood that all matter shown in the accompanying drawings is to be interpreted as illustrative and not in the limiting sense.

Having thus described the invention, there is claimed as new and desired to be secured by Letters Patent:

1. A cervical sampling scraper comprising a planar body including a stem and means for scraping the wall of the cervical canal in the region of the transition zone to obtain a sampling of cells of endocervical origin, said scraping means including a wedge shaped protuberance, the protuberance projecting from one end of the stem, the protuberance including a rounded distal tip, the tip having a diameter approximating the diameter of a normal cervical canal at the cervical portio, the protuberance further including a first straight lateral scraping edge being coincident with an edge of the stem, a second scraping edge extending from the tip at a diverging angle of at least 12° from the first scraping edge and terminating at a base portion of the protuberance, the scraping edges being spaced from one another at the base of the protuberance a distance approximating twice the diameter of the normal cervical canal at the cervical portio and the protuberance extending from the tip to the base a distance of at least one centimeter, limiting means for controlling depth of penetration of the protuberance into the cervical canal, said limiting means including a supportive web projecting laterally from the step adjacent the protuberance, said web having a squamous sampling edge extending substantially transverse to the axis of the stem, said sampling edge having a concave portion being coterminous with the second diverging scraping edge, whereby the protuberance may be fully inserted into and effectively distend a cervical canal with the exertion of a minimal wedge pressure to scrape a deposit of endocervical cell material from the cervical wall with the sampling edge cradling the cervical lip to simultaneously remove a deposit of the squamous material upon rotative manipulation of the stem.

2. A cervical sampling scraper constructed in accordance with claim 1 wherein the squamous sampling edge includes a convex rounded tip, the tip joining the concave portion.

3. A cervical sampling scraper constructed in accordance with claim 2 wherein the squamous tip is spaced from the second scraping edge a distance of approximately 1.5 centimeters, whereby the rotative manipulation of the stem permits the deposit of an adequate sampling of squamous cell material on the web without interference between the web and the walls of the vaginal cavity.

4. A cervical sampling scraper constructed in accordance with claim 1 wherein the stem includes two substantially parallel edges, one of the lateral edges being coincident with one of the scraping edges.

5. A cervical sampling scraper constructed in accordance with claim 1 wherein the angle of divergence lies within a range between 15° and 22°.

6. A cervical sampling scraper constructed in accordance with claim 1 wherein the angle of divergence is no greater than 22°.

7. A cervical sampling scraper constructed in accordance with claim 1 wherein the scraper is formed of one piece wood construction whereby a low cost yet highly efficient cytological sampler is provided.

* * * * *

UNITED STATES PATENT AND TRADEMARK OFFICE
CERTIFICATE OF CORRECTION

PATENT NO. : 4,016,865

DATED : April 12, 1977

INVENTOR(S) : Richard N. Fredricks

It is certified that error appears in the above-identified patent and that said Letters Patent are hereby corrected as shown below:

In claim 1, column 6, line 27, delete "step" and insert --stem--;

In claim 3, column 6, line 45, delete "second" and insert --first--;

In claim 5, column 6, line 57, delete "15°" and insert --12°--.

Signed and Sealed this

Eighteenth Day of October 1977

[SEAL]

Attest:

RUTH C. MASON
*Attesting Officer*

LUTRELLE F. PARKER
*Acting Commissioner of Patents and Trademarks*